United States Patent
Minamida et al.

(10) Patent No.: US 12,174,112 B2
(45) Date of Patent: Dec. 24, 2024

(54) GAS DETECTOR AND LEAKAGE-GAS DETECTION SYSTEM

(71) Applicants: DAIKIN INDUSTRIES, LTD., Osaka (JP); RIKEN, Wako (JP)

(72) Inventors: Tomoatsu Minamida, Osaka (JP); Tomoyuki Haikawa, Osaka (JP); Kazuyuki Satou, Osaka (JP); Satoshi Wada, Wako (JP); Masaki Yumoto, Wako (JP)

(73) Assignees: DAIKIN INDUSTRIES, LTD., Osaka (JP); RIKEN, Saitama (JP)

( * ) Notice: Subject to any disclaimer, the term of this patent is extended or adjusted under 35 U.S.C. 154(b) by 429 days.

(21) Appl. No.: 17/772,064

(22) PCT Filed: Oct. 29, 2020

(86) PCT No.: PCT/JP2020/040668
§ 371 (c)(1),
(2) Date: Apr. 26, 2022

(87) PCT Pub. No.: WO2021/085543
PCT Pub. Date: May 6, 2021

(65) Prior Publication Data
US 2022/0373457 A1    Nov. 24, 2022

(30) Foreign Application Priority Data

Oct. 29, 2019   (JP) .................. 2019-196670
Oct. 28, 2020   (JP) .................. 2020-180465

(51) Int. Cl.
*G01N 21/3504*    (2014.01)
*G01M 3/38*       (2006.01)

(52) U.S. Cl.
CPC .......... *G01N 21/3504* (2013.01); *G01M 3/38* (2013.01)

(58) Field of Classification Search
CPC .......... G01N 21/3504; G01N 33/0049; G01N 2021/1795; G01N 2021/3513; G01N 21/39; G01M 3/228
See application file for complete search history.

(56) References Cited

U.S. PATENT DOCUMENTS

| 4,795,253 A | 1/1989 | Sandridge et al. |
| 2003/0034454 A1 | 2/2003 | Nomura et al. |
| 2021/0108819 A1 | 4/2021 | Chen et al. |

FOREIGN PATENT DOCUMENTS

| JP | 64-78134 A | 3/1989 |
| JP | 4-151546 A | 5/1992 |

(Continued)

OTHER PUBLICATIONS

Harrison ("New infrared absorption cross sections of difluoromethane (HFC-32) for atmospheric remote sensing" Journal of Quantitative Spectroscopy & Radiative Transfer, vol. 270 p. 107639) (Year: 2021).*

(Continued)

*Primary Examiner* — David P Porta
*Assistant Examiner* — Meenakshi S Sahu
(74) *Attorney, Agent, or Firm* — Global IP Counselors, LLP

(57) ABSTRACT

A gas detector detects difluoromethane present in a remote target space. The gas detector includes a detection portion that detects the difluoromethane by using absorption of light of a predetermined wavelength. The predetermined wavelength is in a wavelength range of any of a first wavelength range of 1659 to 1673 nm, a second wavelength range of 1724 to 1726 nm, a third wavelength range of 2218 to 2221 nm, a fourth wavelength range of 2463 to 2466 nm, a fifth wavelength range of 3316 to 3318 nm, and a sixth wavelength range of 9034 to 9130 nm.

16 Claims, 9 Drawing Sheets

(56) References Cited

FOREIGN PATENT DOCUMENTS

| | | | |
|---|---|---|---|
| JP | 10-132737 | A | 5/1998 |
| JP | 2001-235420 | A | 8/2001 |
| JP | 2003-57178 | A | 2/2003 |
| JP | 2008-298638 | A | 12/2008 |
| KR | 20160141590 | A | 12/2016 |
| KR | 101839948 | B1 | 3/2018 |
| WO | 2016/103786 | A1 | 6/2016 |
| WO | 2018/187450 | A1 | 10/2018 |

OTHER PUBLICATIONS

International Search Report of corresponding PCT Application No. PCT/JP2020/040668 dated Dec. 28, 2020.
Kazutoshi Tanabe et al.; "Assessment of Global Warming Risk of Chemical Substances: Prediction of Infrared Absorption Intensity with First-Principle Calculation"; No. 52, pp. 75-81, Table 1; Chiba Institute of Technology, Japan 2005.
International Preliminary Report of corresponding PCT Application No. PCT/JP2020/040668 dated May 12, 2022.
European Search Report of corresponding EP Application No. 20 88 2466.4 dated Nov. 9, 2022.

\* cited by examiner

GAS DETECTOR AND LEAKAGE-GAS DETECTION SYSTEM

CROSS-REFERENCE TO RELATED APPLICATIONS

This U.S. National stage application claims priority under 35 U.S.C. § 119(a) to Japanese Patent Application Nos. 2019-196670 filed in Japan on Oct. 29, 2019 and 2020-180465 filed in Japan on Oct. 28, 2020, the entire contents of which are hereby incorporated herein by reference.

BACKGROUND

Technical Field

The present disclosure relates to a gas detector and a leakage-gas detection system.

Background Art

Japanese Unexamined Patent Application Publication No. 10-132737 discloses a gas-concentration measuring device including a detection-use gas cell for housing a gas to be detected, and a reference-use gas cell for housing a reference-use gas. In this device, a photodetector that receives laser light transmitted through each of the gas cells is used to measure the concentration of a methane gas in the detection-use gas cell.

SUMMARY

Technical Problem

In general, refrigerants circulate in refrigeration apparatuses, such as air conditioners. The refrigerants have a likelihood of leaking out from refrigerant circuits. There is a refrigeration apparatus that uses difluoromethane as a refrigerant. A device that detects the gas concentration of difluoromethane has been demanded for detection of refrigerant leakage.

Conventionally, an infrared absorption spectroscopic device or a semiconductor device that attracts a difluoromethane gas into the device and measures the concentration of the gas is used.

It is, however, difficult for such a device to detect difluoromethane in the vicinity of, for example, a ceiling of a room. If the device is portable, the device can be placed in the vicinity of the ceiling of the room. However, detection work may require long time to detect difluoromethane at a large number of locations in a space in the vicinity of the ceiling.

There is a device that detects a methane gas in a remote place. However, for difluoromethane, there is only a device of a type that attracts a gas into the device.

Solution to Problem

A gas detector according to a first aspect is a gas detector configured to detect difluoromethane present in a remote target space, the gas detector including a detection portion. The detection portion is configured to detect the difluoromethane by using absorption of light of a predetermined wavelength. The predetermined wavelength is in a wavelength range of any of
   a first wavelength range of 1659 to 1673 (nm),
   a second wavelength range of 1724 to 1726 (nm),
   a third wavelength range of 2218 to 2221 (nm),
   a fourth wavelength range of 2463 to 2466 (nm),
   a fifth wavelength range of 3316 to 3318 (nm), and
   a sixth wavelength range of 9034 to 9130 (nm).

A gas detector according to a second aspect is the gas detector according to the first aspect further including an emission portion and a light reception portion. The emission portion is configured to emit first light and second light with respect to the target space. The first light includes infrared of the predetermined wavelength. The second light is light that differs from the first light. The light reception portion is configured to receive the first light and the second light that have passed through the target space. The detection portion is configured to detect the difluoromethane present in the target space on the basis of the first light and the second light received by the light reception portion.

By repeating tests with a latest device having high resolution, the inventor of the present application has recognized the presence of an absorption wavelength range of difluoromethane in a wavelength range the details of which have not been known. Considering this recognition, the inventor of the present application has found that it is possible to detect difluoromethane by emission of the first light including infrared of a wavelength in any of the aforementioned first to fifth wavelength ranges with respect to the target space and reception of the first light and the second light that have passed through the target space by the light reception portion.

A gas detector according to a third aspect is the gas detector according to the second aspect in which the detection portion has a calculation unit. The calculation unit is configured to calculate the concentration of the difluoromethane present in the target space. This calculation of the concentration of the difluoromethane is performed on the basis of a difference between the first light and the second light received by the light reception portion.

Here, it is possible to not only detect the difluoromethane present in the target space but also measure the concentration of the difluoromethane.

A gas detector according to a fourth aspect is a gas detector configured to detect difluoromethane present in a remote target space, the gas detector including an emission portion, a light reception portion, and a detection portion. The emission portion is configured to emit with respect to the target space first light in which a transmission wavelength is modulated by current modulation to include infrared of a predetermined wavelength. The light reception portion is configured to receive the first light that has passed through the target space. The detection portion is configured to detect the difluoromethane present in the target space on the basis of the first light received by the light reception portion. The predetermined wavelength of the infrared included in the first light is in a wavelength range of any of
   a first wavelength range of 1659 to 1673 (nm),
   a second wavelength range of 1724 to 1726 (nm),
   a third wavelength range of 2218 to 2221 (nm),
   a fourth wavelength range of 2463 to 2466 (nm),
   a fifth wavelength range of 3316 to 3318 (nm), and
   a sixth wavelength range of 9034 to 9130 (nm).

The detection portion is configured to detect the difluoromethane present in the target space on the basis of
   a fundamental-wave phase-sensitive detection signal of the predetermined wavelength of the first light, and
   a second-harmonic phase-sensitive detection signal of the predetermined wavelength of the first light or a fourth-harmonic phase-sensitive detection signal of the predetermined wavelength of the first light.

By repeating tests with a latest device having high resolution, the inventor of the present application has recognized the presence of an absorption wavelength of difluoromethane in a wavelength range the details of which have not been known. Considering this recognition, the inventor of the present application has found that it is possible to detect difluoromethane by emission of the first light including infrared of a wavelength in any of the aforementioned first to fifth wavelength ranges with respect to the target space and reception of the first light that has passed through the target space by the light reception portion.

A gas detector according to a fifth aspect is the gas detector according to the fourth aspect in which the detection portion has a calculation unit. The calculation unit is configured to calculate the concentration of the difluoromethane present in the target space on the basis of a ratio of the fundamental-wave phase-sensitive detection signal of the predetermined wavelength of the first light and the second-harmonic phase-sensitive detection signal of the predetermined wavelength of the first light, or a ratio of the fundamental-wave phase-sensitive detection signal of the predetermined wavelength of the first light and the fourth-harmonic phase-sensitive detection signal of the predetermined wavelength of the first light.

Here, it is possible to not only detect the difluoromethane present in the target space but also measure the concentration of the difluoromethane.

A gas detector according to a sixth aspect is the gas detector according to any one of the second aspect to the fifth aspect in which the predetermined wavelength of the infrared of the first light is in a wavelength range of any of the first wavelength range, the second wavelength range, the third wavelength range, and the fourth wavelength range. The light reception portion is configured to receive light reflected or scattered by an object opposite the emission portion with the target space.

Although the light reception portion receives reflected or scattered light, it is possible to detect the difluoromethane with accuracy since absorption into the object is small due to the predetermined wavelength of the first light being in the aforementioned range.

A gas detector according to a seventh aspect is the gas detector according to any one of the second aspect to the fifth aspect in which the predetermined wavelength of the infrared of the first light is in a wavelength range of the fourth wavelength range or the fifth wavelength range. The gas detector according to the seventh aspect further includes a wavelength conversion portion configured to convert a wavelength of light received by the light reception portion into a short wavelength.

With the wavelength conversion portion, thermal noise at the light reception portion is small. It is thus possible to simplify or omit a cooler for removing the thermal noise.

A gas detector according to an eighth aspect is the gas detector according to any one of the second aspect to the fifth aspect in which the predetermined wavelength of the infrared of the first light is in a wavelength range of any of the first wavelength range, the second wavelength range, and the third wavelength range.

Due to the use of the first light of the relatively small wavelength, thermal noise at the light reception portion is small. It is thus possible to simplify or omit a cooler for removing the thermal noise.

In general, a cooler requires time to be started and, when having a large size, degrades convenience of a gas detector.

A gas detector according to a ninth aspect is the gas detector according to any one of the second aspect to the eighth aspect further including a condensing lens or a telescope. The condensing lens or the telescope transmits light that is to be received by the light reception portion.

Even when the amount of light is minute, the light is received by the light reception portion.

As the light condensing lens or the telescope, for example, a Cassegrain telescope is usable.

A leakage-gas detection system according to a tenth aspect includes an air conditioner and the gas detector according to any one of the first aspect to the ninth aspect. The air conditioner has a heat exchanger in which difluoromethane flows as a refrigerant, and a casing that houses the heat exchanger. The gas detector is configured to detect difluoromethane that leaks from the air conditioner into a target space. In the outer surface of the casing of the air conditioner, at least a part that faces the target space has lower absorbance of the infrared than difluoromethane.

The gas detector is used to detect difluoromethane that has leaked from the air conditioner into the target space. As described above, the emission portion of the gas detector emits the first light and the second light with respect to the target space. Thereafter, the first light and the second light that have passed through the target space are received by the light reception portion. Accordingly, if the outer surface of the casing of the air conditioner has high absorbance of infrared, most of the first light is absorbed by the casing of the air conditioner, resulting in a decrease in the amount of the first light received by the light reception portion.

However, in the outer surface of the casing of the air conditioner in the leakage-gas detection system according to the tenth aspect, at least a part that faces the target space has lower absorbance of infrared than difluoromethane. Therefore, the amount of the first light received by the light reception portion is increased, which improves accuracy of detection of difluoromethane.

DETAILED DESCRIPTION OF EMBODIMENT(S)

(1) Need of Portable Gas Detector Capable of Detecting Remote Difluoromethane

Generally, air-conditioning indoor units of a ceiling-installation type are disposed in buildings such as offices, hotels, and commercial facilities. The body of such an air-conditioning indoor unit is installed at an attic, and a blow-out port and an intake port of the air-conditioning indoor unit are disposed in an opening formed in the ceiling. Thus, when difluoromethane as a refrigerant leaks from a cracked portion or a loosened connection portion of a heat exchanger or a refrigerant pipe of the air-conditioning indoor unit, the difluoromethane diffuses into an upper space of the inside of a room from the inside of the air-conditioning indoor unit through the blow-out port and the intake port. As a state in which leaked difluoromethane has diffused into the upper space of the inside of the room, that is, a space below the air-conditioning indoor unit, for example, a state in which the concentration of the difluoromethane in the space is high is expected at the time of refrigerant leakage.

Therefore, for refrigerant leakage from a device such as an air conditioner that uses difluoromethane as a refrigerant, there has been a demand for a gas detector capable of detecting a leakage portion remotely with accuracy.

Conventionally, an existing device attracts a gas with a probe being placed close to a fluorocarbon gas atmosphere and determines the presence/absence and the concentration of fluorocarbon by an infrared absorption spectroscopic method or a semiconductor method. The gas detector is, however, not capable of detecting a remote gas.

(2) Leakage-Gas Detection System

Figure 1:
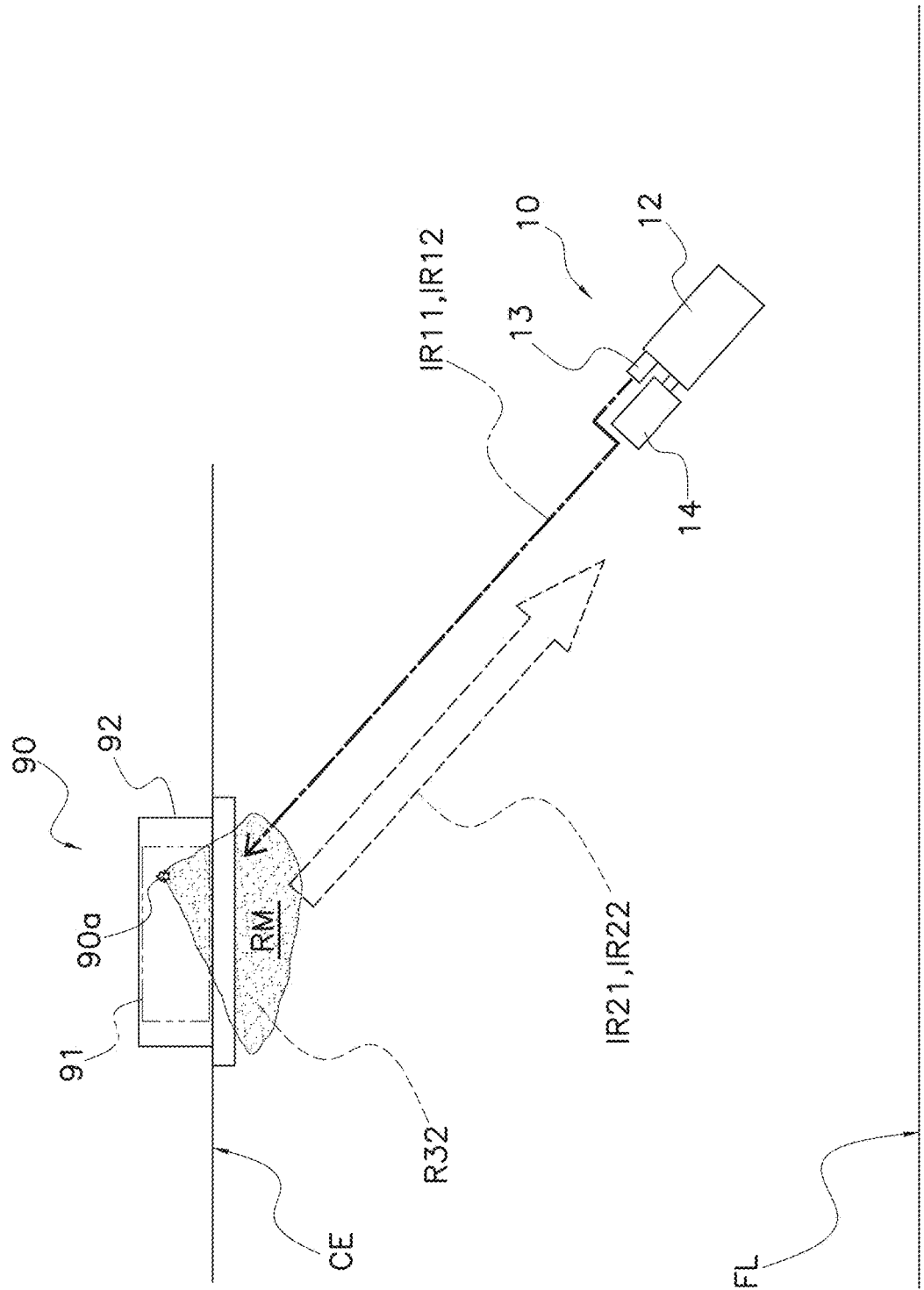
FIG. 1 is a schematic view of a leakage-gas detection system including a gas detector.

In FIG. 1, a leakage-gas detection system is illustrated. The leakage-gas detection system includes an air conditioner 90 of a ceiling-installation type and a gas detector 10. The air conditioner 90 has a heat exchanger 91 in which difluoromethane (R32) flows as a refrigerant, and a casing 92 that houses the heat exchanger 91. The gas detector 10 detects difluoromethane that leaks from the air conditioner 90 into a target space RM. The target space RM is an indoor space of a room in which the air conditioner 90 is installed, the space being surrounded by a ceiling CE, a side wall, and a floor FL.

In the outer surface of the casing 92 of the air conditioner 90, at least a part that faces the target space RM has lower absorbance of infrared than difluoromethane. Specifically, the absorbance of infrared is suppressed to be low by forming a panel of the casing 92 exposed to the inside of the room with a material that includes metal powder or subjecting a surface of the panel to plating. The outer surface of the casing 92 is a solid body. The casing 92 thus has low absorbance of infrared even without using metal powder or being subjected to plating.

The gas detector 10, which will be described later, is a portable device and is to be carried by a service person for detecting refrigerant leakage. The gas detector 10 emits infrared with respect to the target space RM below the air conditioner 90 away from the gas detector 10, receives light reflected or scatted by the casing 92 of the air conditioner 90 and the ceiling CE, and performs a calculation, thereby detecting the presence and the concentration of difluoromethane in the target space RM.

(3) Configuration of Gas Detector

Figure 2:
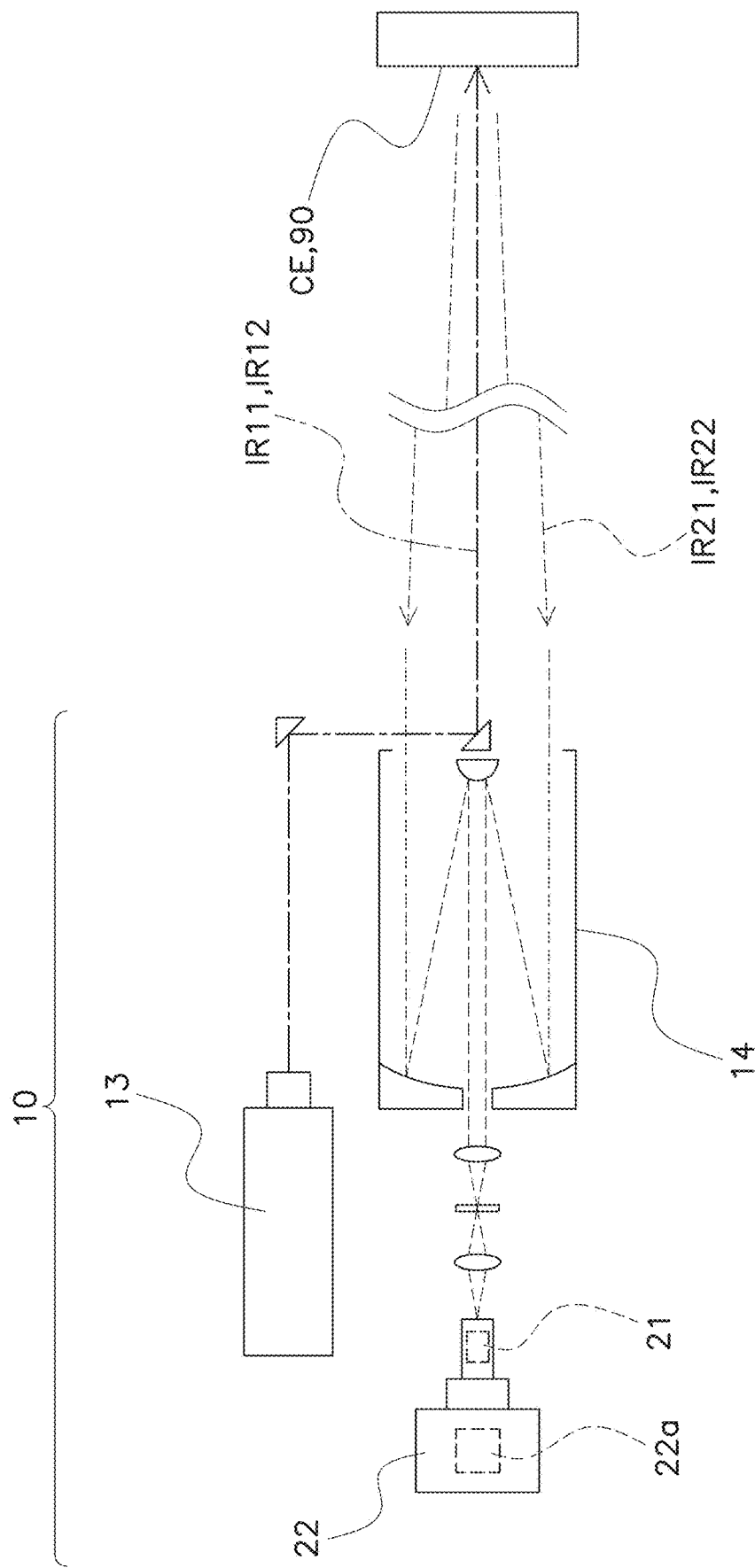
FIG. 2 is a schematic view of a gas detector.

The gas detector 10 illustrated in FIG. 2 is a gas detector based on a laser sensing technology and includes a body 12, an emission portion 13, and a condensing cylinder 14.

The emission portion 13 emits first light IR11, which is laser light, and second light IR12 with respect to the target space RM. The first light IR11 includes infrared of a predetermined wavelength. The second light IR12 is light that differs from the first light IR11.

The predetermined wavelength of the infrared included in the first light IR11 is in a wavelength range of 1659 to 1673 (nm).

The second light IR12 is near infrared that is near infrared (700 to 2500 (nm)) of a wavelength band other than a first wavelength range of 1659 to 1673 (nm), a second wavelength range of 1724 to 1726 (nm), a third wavelength range of 2218 to 2221 (nm), and a fourth wavelength range of 2463 to 2466 (nm).

As described later, when difluoromethane is present in the target space RM, part of the first light IR11 is absorbed, and the second light IR12 is not absorbed.

The condensing cylinder 14 is a condensing lens or a telescope and transmits light received by a light reception portion 21, which will be described later. A Cassegrain telescope is employed as the condensing cylinder 14.

At the body 12, the light reception portion 21 and a detection portion 22 are disposed.

Via the condensing cylinder 14, the light reception portion 21 receives the first light and the second light (hereinafter referred to as the reflection light IR21 and IR22) that have passed through the target space RM and reflected or scattered by the casing 92 of the air conditioner 90 and the ceiling CE. The light reception portion 21 is an infrared detection element that receives infrared and converts the infrared into an electrical signal. A MCT (HgCdTe) infrared detection element is employed as an infrared detection element.

On the basis of the reflection light IR21 and IR22 received by the light reception portion 21, the detection portion 22 detects difluoromethane present in the target space RM. The detection portion 22 has a signal amplifier and a calculation unit 22a.

The calculation unit 22a is realized by a computer. The calculation unit 22a includes a control calculation device and a storage device. A processor such as a CPU or a GPU is usable for the control calculation device. The control calculation device reads a program stored in the storage device and performs a predetermined image processing and a predetermined calculation processing in accordance with the program. In addition, the control calculation device can write a calculation result in the storage device in accordance with a program and read information stored in the storage device.

The calculation unit 22a receives an electrical signal from the light reception portion 21 and calculates the concentration of difluoromethane present in the target space RM. This calculation of the concentration of difluoromethane is performed on the basis of a difference between the reflection light (the first light and the second light) IR21 and IR22 received by the light reception portion 21.

(4) Operation of Gas Detector

By using the portable gas detector 10 carried by a service person, the leakage-gas detection system examines whether a refrigerant (difluoromethane) has leaked from the air conditioner 90 installed at the ceiling CE of a room in a building, such as an office. The service person determines as the target space RM (refer to FIG. 1) for gas detection a space below the air conditioner 90 in the vicinity of the ceiling CE and causes laser light (the first light IR11 and the second light IR12) to be emitted toward the target space RM.

As illustrated in FIG. 1, if difluoromethane (R32) has leaked from a cracked portion 90a of the heat exchanger 91 or a refrigerant pipe of the air conditioner 90, difluoromethane of a predetermined concentration should be present in the target space RM. In the laser light, part of the first light IR11 is absorbed by difluoromethane, and the second light IR12 is not absorbed by difluoromethane. Accordingly, regarding the reflection light (the first light and the second light) IR21 and IR22 from the casing 92 of the air conditioner 90 and the ceiling CE, a difference is generated in the detection level at the light reception portion 21. On the basis of this difference, the calculation unit 22a calculates the concentration of the difluoromethane in the target space RM.

As illustrated in FIG. 2, the reflection light (the first light and the second light) IR21 and IR22 enters the light reception portion 21 via the condensing cylinder 14. The condensing cylinder 14 widely condenses reflected or scattered light. Accordingly, the light reception portion 21 can detect even the reflection light (the first light) IR21 that has been absorbed to become a minute amount.

(5) Characteristics of Absorbance of Infrared of Difluoromethane

By repeating tests with a latest device having high resolution, the inventor of the present application has recognized the presence of an absorption wavelength range of difluoromethane in a wavelength range the details of which have not been known.

Figure 3:
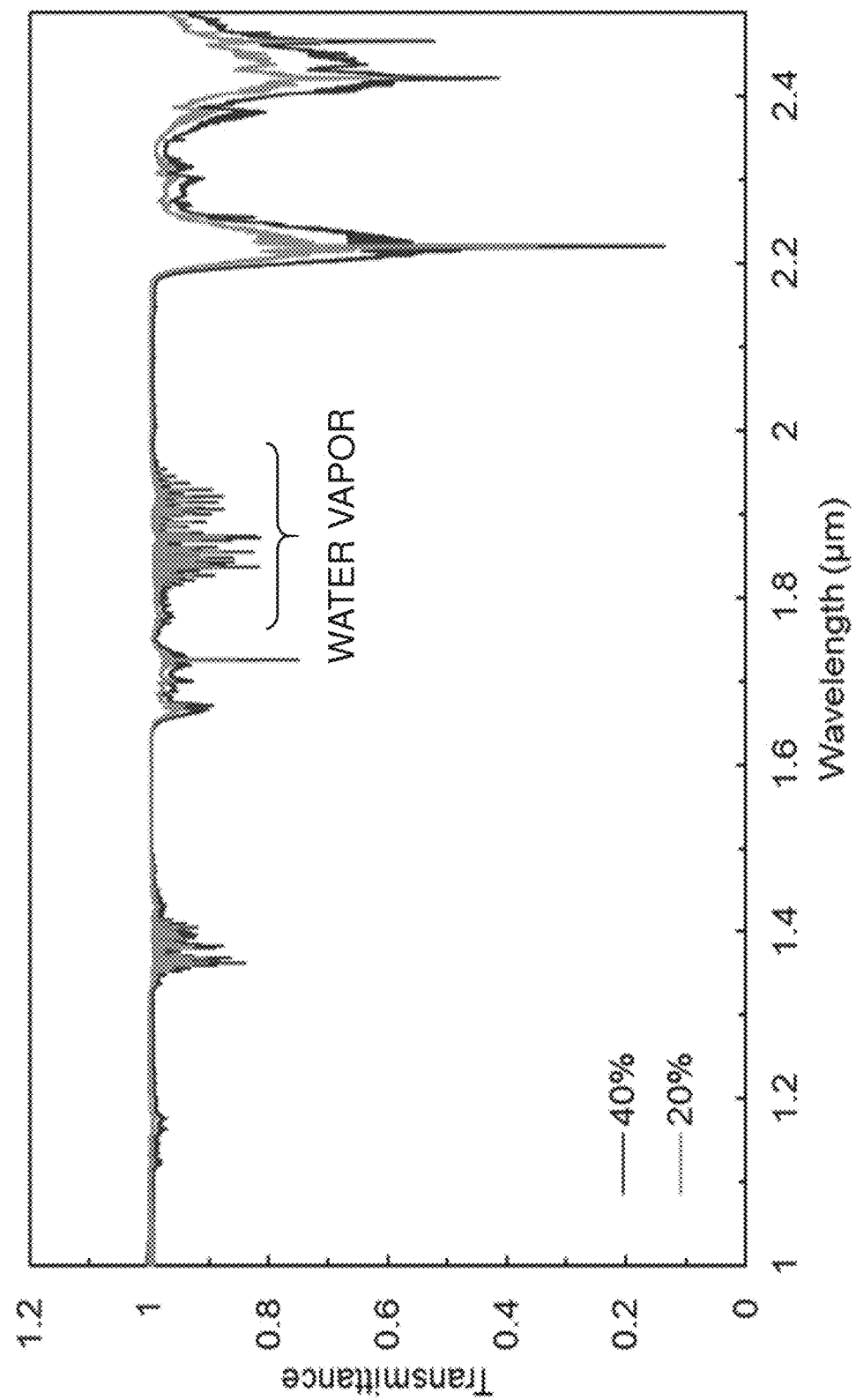
FIG. 3 is a graph showing transmittance of infrared regarding difluoromethane in a wavelength band of 2 μm to 10 μm (2000 nm to 10000 nm).
Figure 4:
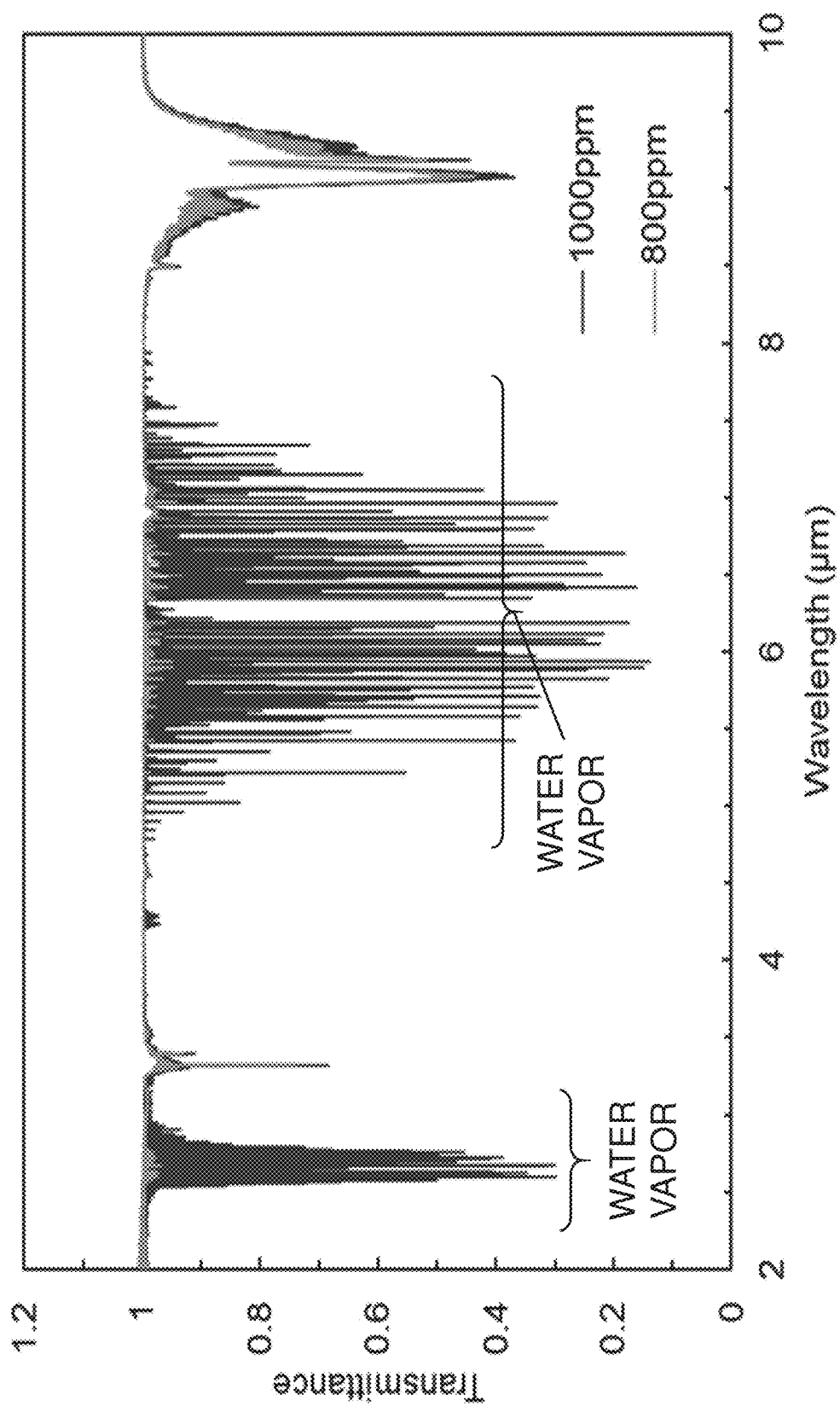
FIG. 4 is a graph showing transmittance of infrared regarding difluoromethane in a wavelength band of 1 μm to 2.5 μm (1000 nm to 2500 nm).
Figure 5:
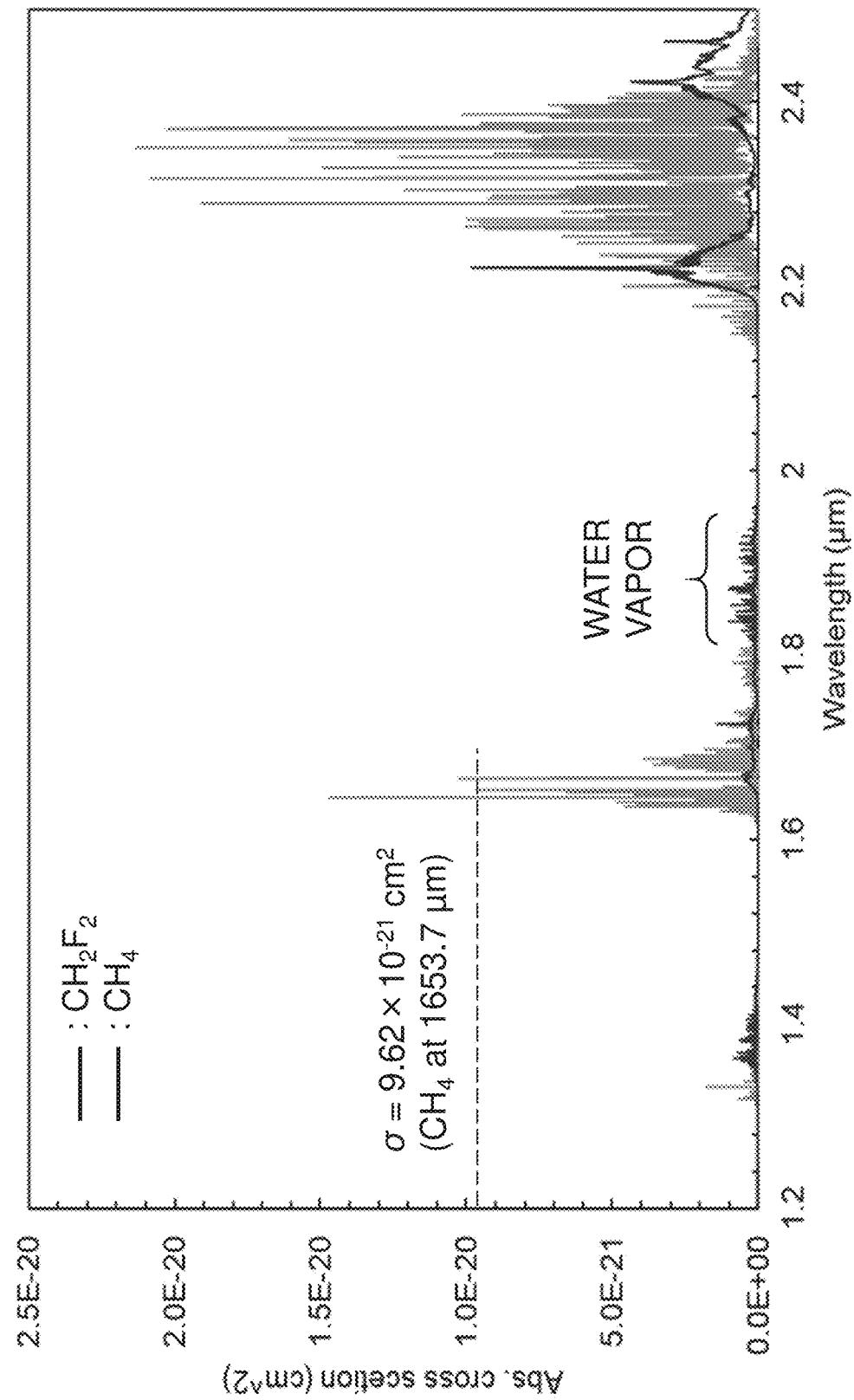
FIG. 5 is a graph showing infrared-absorption cross sections of difluoromethane and methane in a wavelength band of 1.2 μm to 2.5 μm (1200 nm to 2500 nm).
Figure 6:
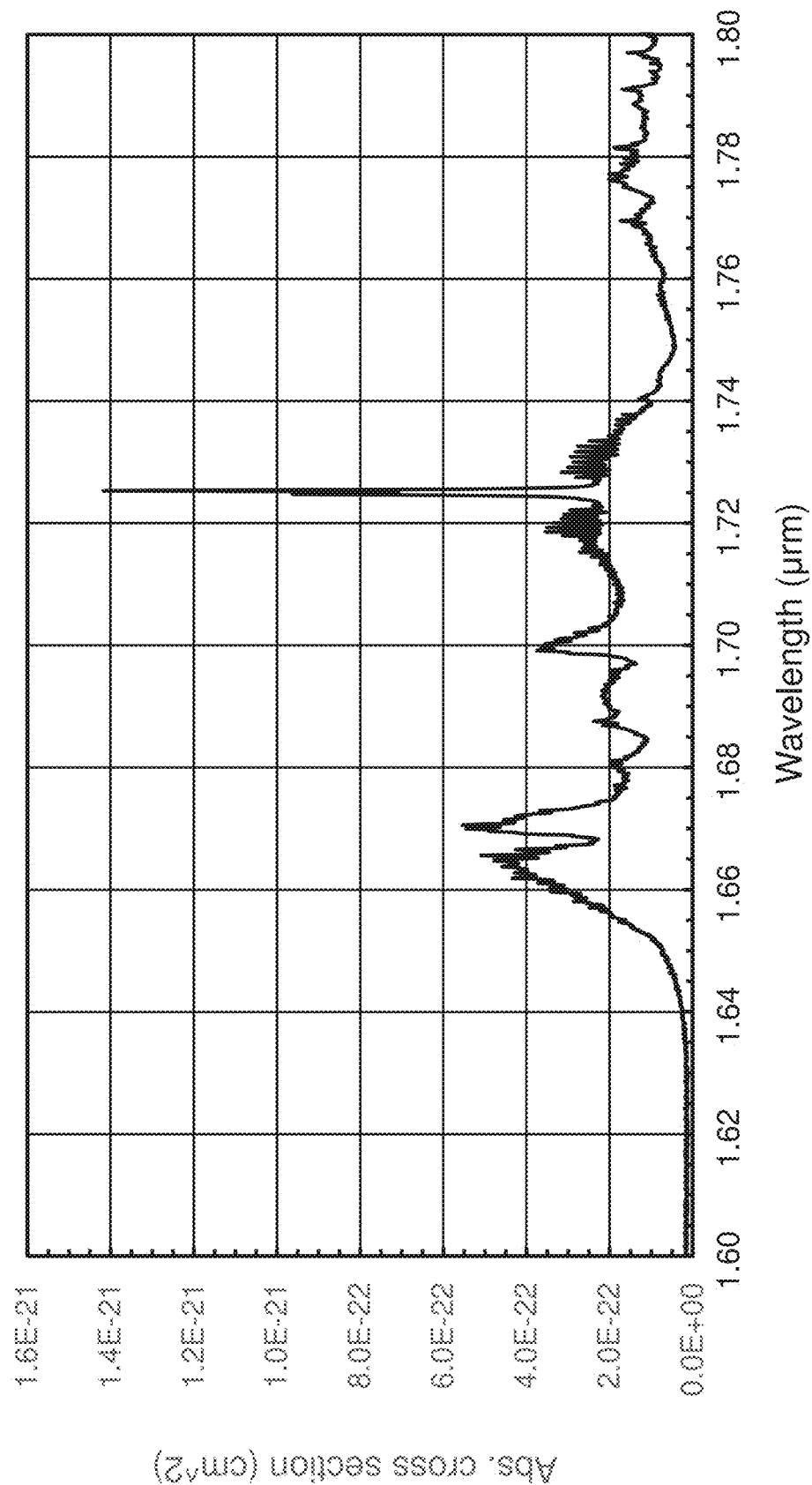
FIG. 6 is a graph showing infrared-absorption cross sections of difluoromethane in a wavelength band of 1.6 μm to 1.8 μm (1600 nm to 1800 nm).
Figure 7:
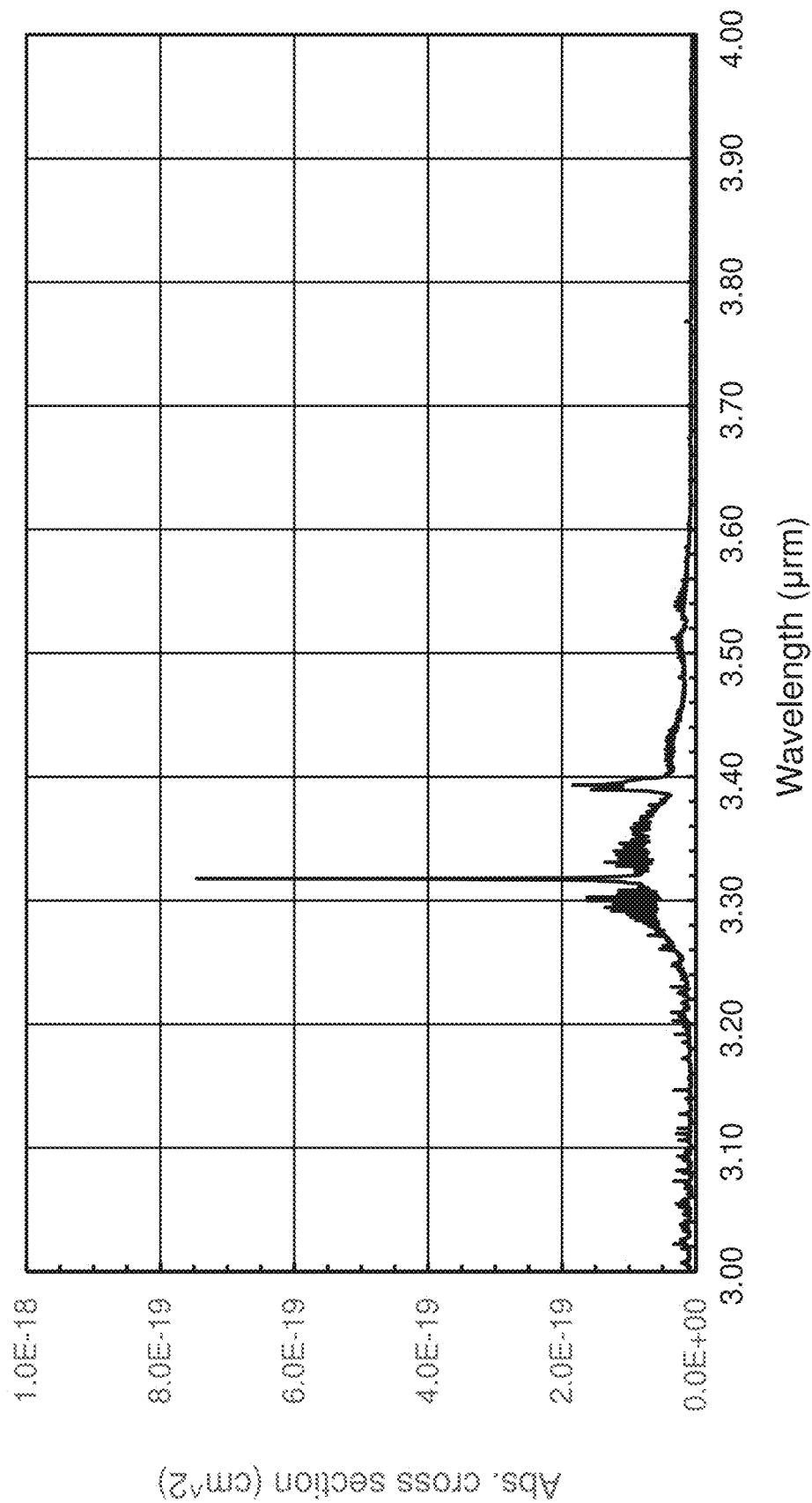
FIG. 7 is a graph showing infrared-absorption cross sections of difluoromethane in a wavelength band of 2.1 μm to 2.5 μm (2100 nm to 2500 nm).
Figure 8:
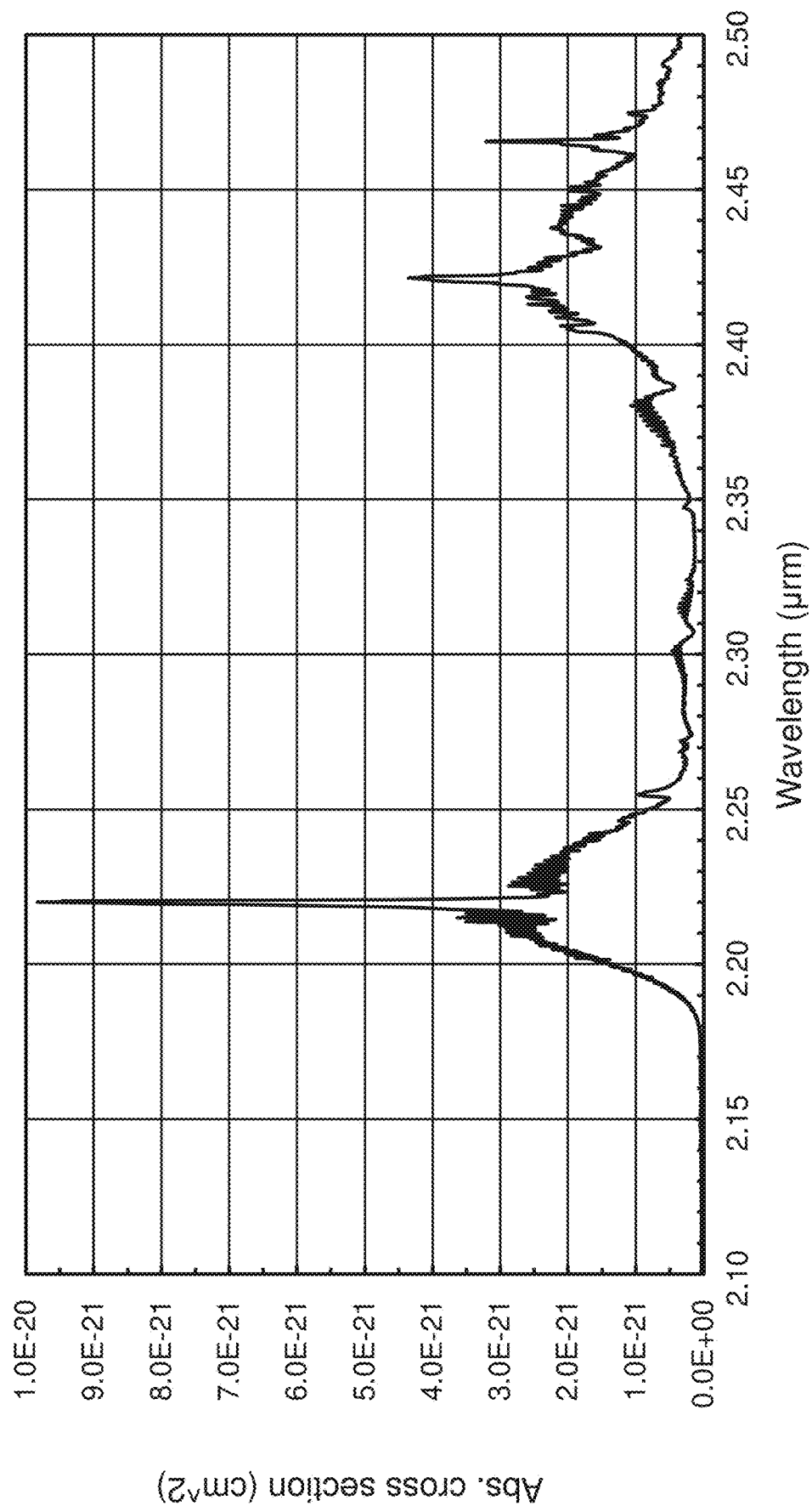
FIG. 8 is a graph showing infrared-absorption cross sections of difluoromethane in a wavelength band of 3.0 μm to 4.0 μm (3000 nm to 4000 nm).
Figure 9:
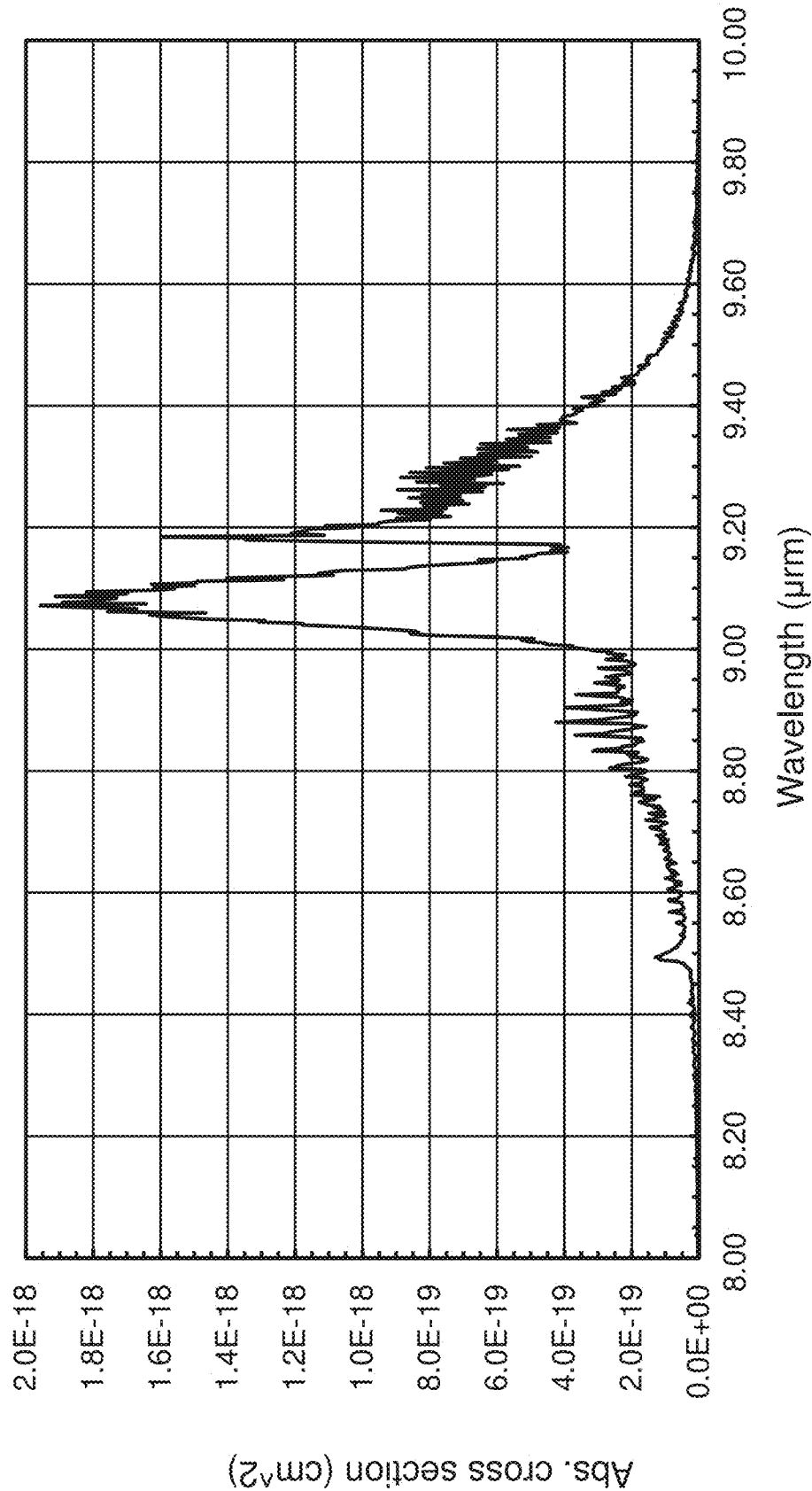
FIG. 9 is a graph showing infrared-absorption cross sections of difluoromethane in a wavelength band of 8.0 μm to 10.0 μm (8000 nm to 10000 nm).

FIG. 3 and FIG. 4 are graphs in which wavelengths of infrared are plotted on the horizontal axis and transmittances of infrared of each wavelength at a time when passing through a space in which difluoromethane of a predetermined concentration is present are plotted on the vertical axis. FIG. 5 is a graph in which wavelengths of infrared are plotted on the horizontal axis and absorption cross sections of methane and difluoromethane are plotted on the vertical axis. As shown in these graphs, knowledge of the presence of absorption wavelengths of difluoromethane, in particular, in bands of near infrared and mid infrared and transmittances and absorption cross sections thereof has been obtained as a result of tests. Specifically, knowledge of the presence of the following five absorption wavelength ranges and absorption cross sections at the peak of each absorption wavelength range has been obtained.

The absorption cross section is $5.5 \times 10^{-22}$ cm$^2$ in the first wavelength range of 1659 to 1673 (nm).
The absorption cross section is $1.4 \cdot 10^{-21}$ cm$^2$ in the second wavelength range of 1724 to 1726 (nm).
The absorption cross section is $9.8 \cdot 10^{-21}$ cm$^2$ in the third wavelength range of 2218 to 2221 (nm).
The absorption cross section is $3.2 \times 10^{-21}$ cm$^2$ in the fourth wavelength range of 2463 to 2466 (nm).
The absorption cross section is $7.5 \times 10^{-19}$ cm$^2$ in the fifth wavelength range of 3316 to 3318 (nm).
The absorption cross section is $2.0 \times 10^{-18}$ cm$^2$ in the sixth wavelength range of 9034 to 9130 (nm).

On the basis of such new knowledge, the aforementioned gas detector 10 employs as the first light IR11 infrared in a wavelength range of 1659 to 1673 (nm) and is configured to perform emission toward the target space RM from the emission portion 13.

As obvious from the graph in FIG. 5, it is found that the absorption cross section of difluoromethane (R32) in a band of 1.6 to 2.5 μm is extremely small compared with methane (CH$_4$). It is, however, possible for the gas detector 10 to detect difluoromethane present in the remote target space RM when the difluoromethane has a concentration of a certain degree or more.

The infrared wavelength region with a note "water vapor" in FIG. 3 to FIG. 5 is an infrared wavelength region in which it is difficult to remove the presence of water vapor in the system of a measuring device such as a gas cell. In the measurement results indicated in FIG. 3 to FIG. 5, characteristics of water vapor are also present. FIG. 3 to FIG. 5 include the note "water vapor" to avoid confusion with characteristics of difluoromethane and methane.

(6) Features
(6-1)

As described above, the inventor of the present application has found by repeating tests that an absorption wavelength of difluoromethane is present also in a wavelength range (1600 nm to 2500 nm) that has not been recognized. In the gas detector 10 according to the aforementioned embodiment, the wavelength of the first light IR11 is set to 1659 to 1673 (nm) to enable detection of difluoromethane present in the remote target space RM.

It has not been possible in tests in which a previous measuring device having low resolution is used to find the absorption wavelength of difluoromethane that has not been recognized. As a result of repeated tests using a latest measuring device having high resolution, the knowledge illustrated in FIG. 3 to FIG. 5 can be obtained.

(6-2)

In the gas detector 10, the wavelength of the first light IR11 is set to 1659 to 1673 (nm) included in the wavelength region of near infrared (electromagnetic waves having a wavelength of 700 to 2500 (nm)). Therefore, compared with when mid infrared (2500 to 4000 (nm)) or far infrared (4000 (nm) or more) is selected, it is possible to omit or simplify cooling for removing thermal noise. Consequently, manufacturing costs are reduced. In addition, it is possible to suppress degradation of convenience due to a time from when the cooler is started to when the cooler becomes stable.

To perform minimum required cooling, for example, a peltier element is usable as a cooler of the infrared detection element.

(6-3)

In the gas detector 10, the light reflected or scattered by an object (the air conditioner 90, the ceiling CE, and the like) opposite the emission portion 13 with the target space RM is received by the light reception portion 21. Therefore, the emission portion 13 and the light reception portion 21 can be close to each other, which makes the gas detector 10 easily portable.

(6-4)

In general, the absorption wavelengths of building materials and structures of buildings are in, for example, a band near 3 μm in the case of PP (polypropylene), PS (polystyrene), ABS (acrylonitrile butadiene styrene), AS (acrylonitrile styrene), and the like and are in, for example, a band near 9 μm in the case of PS (polystyrene), paper of ceiling surfaces, wood materials, and the like. If the wavelength of infrared that is to be emitted from the gas detector is selected from a band near 3 μm, near 9 μm, or the like, the presence of a difluoromethane gas may be incorrectly recognized due to light absorption by building materials and structures when the wavelength does coincide with the absorption wavelengths of the building materials and the structures or when the absorption cross section is not sufficiently small compared with the difluoromethane gas.

In the gas detector 10, however, the wavelength of the first light IR11 is set to 1659 to 1673 (nm). Therefore, the influence of light absorption by building materials and structures is small.

(6-5)

The aforementioned leakage-gas detection system uses the gas detector 10 to detect difluoromethane that has leaked from the air conditioner 90 into the target space RM. As described above, the emission portion 13 of the gas detector 10 emits the first light IR11 and the second light IR12 with respect to the target space RM. Thereafter, the first light (the reflection light IR21) and the second light (reflection light IR22) that have passed through the target space RM are received by the light reception portion 21. Accordingly, if the outer surface of the casing 92 of the air conditioner 90 has high absorbance of infrared, most of the first light IR11 is absorbed by the casing 92 of the air conditioner 90, resulting in a decrease in the amount of light received by the light reception portion 21.

However, in the outer surface of the casing 92 of the air conditioner 90 in the aforementioned leakage-gas detection system, at least the part that faces the target space RM has lower absorbance of infrared than difluoromethane. Specifically, it is possible to take a measure of forming a panel of the casing 92 exposed to the inside of a room with a material that includes metal powder or subjecting a surface of the panel to plating.

Therefore, the received amount of reflected or scattered light in the gas detector 10 is increased, which increases accuracy of detection of difluoromethane.

Even without taking the measure of forming with a material that includes metal powder or subjecting a surface of the panel to plating, the casing 92 has low absorbance of infrared since the outer surface of the casing 92 is a solid body.

(7) Modifications (7-1) Modification 1A

In the aforementioned gas detector 10, the predetermined wavelength of the infrared included in the first light IR11 is set in the wavelength range of 1659 to 1673 (nm).

As an alternative to this, the wavelength of the first light may be set in the wavelength range of 1724 to 1726 (nm), 2218 to 2221 (nm), or 2463 to 2466 (nm). As described above, infrared in these wavelength ranges also coincides with the absorption wavelength of difluoromethane and is easily absorbed by the difluoromethane. Therefore, favorable accuracy of the detection of the difluoromethane is expected.

The wavelength range of 1724 to 1726 (nm), 2218 to 2221 (nm), or 2463 to 2466 (nm) is also in the wavelength region of near infrared, and cooling for removing thermal noise can be omitted or simplified.

(7-2) Modification 1B

In the aforementioned gas detector 10, the predetermined wavelength of the infrared included in the first light IR11 is set in the wavelength range of 1659 to 1673 (nm).

As an alternative to this, the wavelength of the first light may be set in the wavelength range of 3316 to 3318 (nm). In this case, although there are some demerits, such as that cooling is required for removing thermal noise, the absorption cross section of difluoromethane is large ($7.5 \times 10^{-19}$ $cm^2$), as described above. Accordingly, compared with when near infrared is employed as the first light, it is possible to detect difluoromethane of a lower concentration.

(7-3) Modification 1C

In the aforementioned gas detector 10, the predetermined wavelength of the infrared included in the first light IR11 is set in the wavelength range of 1659 to 1673 (nm).

As an alternative to this, the wavelength of the first light may be set in the wavelength range of 9034 to 9130 (nm). Also in this case, as in Modification 1B, there are some demerits, such as that cooling for removing thermal noise is required. However, the absorption cross section of difluoromethane is larger ($2.0 \times 10^{-18}$ $cm^2$), as described above. Accordingly, compared with when near infrared is employed as the first light, it is possible to detect difluoromethane of a lower concentration.

(7-4) Modification 1D

In the aforementioned gas detector 10, a configuration in which the emission portion 13 emits the first light IR11 and the second light IR12 is employed.

As an alternative to this, a configuration in which the emission portion emits only the first light can be employed. In this case, the emission portion emits with respect to the target space the first light in which the transmission wavelength is modulated by current modulation to include infrared of a predetermined wavelength. The detection portion detects difluoromethane present in the target space on the basis of a fundamental-wave phase-sensitive detection signal of a predetermined wavelength of the first light and a second-harmonic phase-sensitive detection signal of a predetermined wavelength of the first light.

When the predetermined wavelength of the first light is set in the wavelength range of 1659 to 1673 (nm), it is preferable to use a fourth-harmonic phase-sensitive detection signal of the predetermined wavelength of the first light instead of the second-harmonic phase-sensitive detection signal of the predetermined wavelength of the first light. Specifically, the detection portion calculates the concentration of difluoromethane on the basis of a ratio of the fundamental-wave phase-sensitive detection signal of the predetermined wavelength of the first light and the fourth-harmonic phase-sensitive detection signal of the predetermined wavelength of the first light. This is because the wavelength range of 1659 to 1673 (nm) includes two peaks, differently from the other ranges of the absorption wavelength of difluoromethane, such as the ranges of 1724 to 1726 (nm), 2218 to 2221 (nm), and 2463 to 2466 (nm). If fundamental-wave phase-sensitive detection vibration is emitted in the entirety of the wavelength range of 1659 to 1673 (nm), a fourth harmonic is to be detected. Thus, the fourth-harmonic phase-sensitive detection signal is used instead of the second-harmonic phase-sensitive detection signal.

(7-5) Modification 1E

As in Modification 1B and Modification 1C described above, when mid infrared or far infrared is to be emitted as the first light from the emission portion, the gas detector is preferably further provided with a wavelength conversion portion. It is possible to simplify the measures for thermal noise by configuring such that the wavelength of reflected or scattered light is converted by the wavelength conversion portion and the light whose wavelength has been converted is received by the light reception portion.

As the wavelength conversion portion, a wavelength conversion device such as a non-liner optical crystal can be employed.

(7-6) Modification 1F

In the aforementioned gas detector 10, a configuration in which the emission portion 13 emits the first light IR11 and the second light IR12 is employed.

As an alternative to this, the wavelength may be changed by changing the output of laser from the emission portion, and light of two wavelengths may be detected by extracting and inserting a wavelength selection film. The wavelength selection film is extracted or inserted on the front side of the detector.

Instead of extraction and insertion of the wavelength selection film, wavelength conversion crystal such as lithium niobate (PPLN) may be used. When wavelength conversion, for example, from mid infrared to visible light or to near infrared can be performed by using the wavelength conversion crystal, cooling using liquid nitrogen or the like is not necessary, and it is possible to detect difluoromethane without thermal noise at a room temperature.

As a light source of the emission portion, an LED may be employed instead of laser. In this case, by using the multiple wavelengths of LED light oscillated from the emission portion, it is possible to detect difluoromethane by dispersing light with half mirror and calculating a difference between two wavelengths.

(7-7) Modification 1G

In the aforementioned leakage-gas detection system, a space around the air conditioner 90 is considered as the target space RM, and emission from the emission portion 13 of the gas detector 10 is performed with respect to the space.

If the air conditioner is installed at a side wall of a room in a building, a refrigerant (difluoromethane) that leaks from the air conditioner diffuses into a space in the vicinity of the side wall. Thus, the target space is a space along the side wall, not near a ceiling. If the air conditioner is of a floor installation type, the target space is a space near a floor surface.

(Additional Note)

Embodiments of a gas detector and a leakage-gas detection system have been described above; however, it should be understood that various changes in the forms and the details are possible without departing from the gist and the scope of the present disclosure described in the claims.

What is claimed is:

1. A gas detector configured to detect difluoromethane present in a remote target space, the gas detector comprising:
    a detection portion configured to detect the difluoromethane by using absorption of light of a predetermined wavelength,
    the predetermined wavelength being in a wavelength range of any of
       a first wavelength range of 1659 to 1673 nm,
       a second wavelength range of 1724 to 1726 nm,
       a third wavelength range of 2218 to 2221 nm,
       a fourth wavelength range of 2463 to 2466 nm,
       a fifth wavelength range of 3316 to 3318 nm, and
       a sixth wavelength range of 9034 to 9130 nm.

2. The gas detector according to claim 1, further comprising:
    an emission portion configured to emit, with respect to the remote target space,
       first light that includes infrared light of the predetermined wavelength and
       second light that differs from the first light; and
    a light reception portion configured to receive the first light and the second light that have passed through the remote target space,
    the detection portion being configured to detect the difluoromethane present in the remote target space based on the first light and the second light received by the light reception portion.

3. The gas detector according to claim 2, wherein
    the detection portion includes a calculation unit, and
    the calculation unit is configured to calculate a concentration of the difluoromethane present in the remote target space based on
       a difference between the first light and the second light received by the light reception portion.

4. A gas detector configured to detect difluoromethane present in a remote target space, the gas detector comprising:
    an emission portion configured to emit, with respect to the remote target space, first light in which a transmission wavelength is modulated by current modulation to include infrared light of a predetermined wavelength;
    a light reception portion configured to receive the first light that has passed through the remote target space; and
    a detection portion configured to detect the difluoromethane present in the remote target space based on the first light received by the light reception portion,
    the predetermined wavelength being in a wavelength range of any of
       a first wavelength range of 1659 to 1673 nm,
       a second wavelength range of 1724 to 1726 nm,
       a third wavelength range of 2218 to 2221 nm,
       a fourth wavelength range of 2463 to 2466 nm,
       a fifth wavelength range of 3316 to 3318 nm, and
       a sixth wavelength range of 9034 to 9130 nm, and
    the detection portion being configured to detect the difluoromethane present in the remote target space based on
       a fundamental-wave phase-sensitive detection signal of the predetermined wavelength of the first light, and
       a second-harmonic phase-sensitive detection signal of the predetermined wavelength of the first light or a fourth-harmonic phase-sensitive detection signal of the predetermined wavelength of the first light.

5. The gas detector according to claim 4, wherein
    the detection portion includes a calculation unit, and
    the calculation unit is configured to calculate a concentration of the difluoromethane present in the remote target space based on
       a ratio of the fundamental-wave phase-sensitive detection signal of the predetermined wavelength of the first light to the second-harmonic phase-sensitive detection signal of the predetermined wavelength of the first light, or
       a ratio of the fundamental-wave phase-sensitive detection signal of the predetermined wavelength of the first light to the fourth-harmonic phase-sensitive detection signal of the predetermined wavelength of the first light.

6. The gas detector according to claim 2, wherein
    the predetermined wavelength is in a wavelength range of any of the first wavelength range, the second wavelength range, the third wavelength range, and the fourth wavelength range, and
    the light reception portion is configured to receive light reflected or scattered by an object opposite the emission portion within the remote target space.

7. The gas detector according to claim 2, further comprising:
    a wavelength conversion portion configured to convert a wavelength of light received by the light reception portion,
    the predetermined wavelength being in a wavelength range of the fourth wavelength range or the fifth wavelength range.

8. The gas detector according to claim 2, wherein
    the predetermined wavelength is in a wavelength range of any of the first wavelength range, the second wavelength range, and the third wavelength range.

9. The gas detector according to claim 2, further comprising:
a condensing lens or a telescope configured to transmit light that is to be received by the light reception portion.

10. A leakage-gas detection system including the gas detector according the claim 2, the leakage-gas detection system further comprising:
an air conditioner having
a heat exchanger in which the difluoromethane flows as a refrigerant, and
a casing that houses the heat exchanger,
the gas detector being configured to detect difluoromethane that leaks from the air conditioner into the remote target space,
in an outer surface of the casing, at least a part that faces the remote target space having lower absorbance of the infrared light than the difluoromethane.

11. The gas detector according to claim 4, wherein
the predetermined wavelength is in a wavelength range of any of the first wavelength range, the second wavelength range, the third wavelength range, and the fourth wavelength range, and
the light reception portion is configured to receive light reflected or scattered by an object opposite the emission portion within the remote target space.

12. The gas detector according to claim 4, further comprising:
a wavelength conversion portion configured to convert a wavelength of light received by the light reception portion,
the predetermined wavelength being in a wavelength range of the fourth wavelength range or the fifth wavelength range.

13. The gas detector according to claim 4, wherein
the predetermined wavelength is in a wavelength range of any of the first wavelength range, the second wavelength range, and the third wavelength range.

14. The gas detector according to claim 4, further comprising:
a condensing lens or a telescope configured to transmit light that is to be received by the light reception portion.

15. A leakage-gas detection system including the gas detector according the claim 4, the leakage-gas detection system further comprising:
an air conditioner having
a heat exchanger in which the difluoromethane flows as a refrigerant, and
a casing that houses the heat exchanger,
the gas detector being configured to detect difluoromethane that leaks from the air conditioner into the remote target space,
in an outer surface of the casing, at least a part that faces the remote target space having lower absorbance of the infrared light than the difluoromethane.

16. A leakage-gas detection system including the gas detector according the claim 1, the leakage-gas detection system further comprising:
an air conditioner having
a heat exchanger in which the difluoromethane flows as a refrigerant, and
a casing that houses the heat exchanger,
the gas detector being configured to detect difluoromethane that leaks from the air conditioner into the remote target space,
in an outer surface of the casing, at least a part that faces the remote target space having lower absorbance of the infrared light than the difluoromethane.

* * * * *